(12) United States Patent
Uetani et al.

(10) Patent No.: US 6,348,297 B1
(45) Date of Patent: Feb. 19, 2002

(54) CHEMICAL AMPLIFICATION TYPE POSITIVE RESIST

(75) Inventors: Yasunori Uetani, Toyonaka; Kenji Oohashi, Yawata; Hiroki Inoue, Toyonaka, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/533,986

(22) Filed: Mar. 24, 2000

(30) Foreign Application Priority Data

Mar. 31, 1999 (JP) .......................... 11-092990
Nov. 5, 1999 (JP) .......................... 11-315264

(51) Int. Cl.$^7$ ............................................ G03F 7/004
(52) U.S. Cl. ................... 430/270.1; 430/914; 430/921; 568/28; 568/35; 568/77
(58) Field of Search ............................ 430/270.1, 914, 430/921; 568/28, 35, 77

(56) References Cited

U.S. PATENT DOCUMENTS

| | | | |
|---|---|---|---|
| 5,558,971 A | 9/1996 | Urano et al. ............. | 430/270.1 |
| 5,558,976 A | 9/1996 | Urano et al. ............. | 430/326 |
| 5,585,507 A | 12/1996 | Nakano et al. ............. | 556/7 |
| 5,635,332 A | 6/1997 | Nakano et al. ........... | 430/270.1 |
| 5,667,943 A | * 9/1997 | Boggs et al. ............... | 430/343 |
| 5,691,111 A | 11/1997 | Iwasa et al. ............. | 430/270.1 |
| 5,756,850 A | 5/1998 | Iwasa et al. ................ | 568/75 |
| 5,817,444 A | * 10/1998 | Sato et al. .................. | 430/155 |
| 5,968,713 A | 10/1999 | Nozaki et al. ............. | 430/326 |
| 6,013,416 A | 1/2000 | Nozaki et al. ........... | 430/270.1 |

FOREIGN PATENT DOCUMENTS

| | | |
|---|---|---|
| EP | 0856773 A1 | 5/1998 |
| EP | 0856773 A1 | 8/1998 |
| JP | 7092675 | 4/1995 |
| JP | 1073919 | 3/1998 |
| JP | 10133371 | 5/1998 |
| JP | 10319595 | 12/1998 |

OTHER PUBLICATIONS

Takechi, et al., *Journal of Photopolymer Science and Technology*, vol. 9, No. 3, 1996, pp. 475–488.
Hofer, et al, *Journal of Photopolymer Science and Technology*, vol. 9, No. 3, 1996, pp. 387–398.
Y Uetani et al., *International Society for Optical Engineering*, vol. 3678, No. 1, 1999 p. 512, paragraph 2.3.

* cited by examiner

Primary Examiner—Rosemary Ashton

(74) Attorney, Agent, or Firm—Birch, Stewart, Kolasch & Birch, LLP

(57) ABSTRACT

A chemical amplification type positive resist composition which is good in resolution, provide a good pattern profile under exposure using light of wavelength of 220 nm or shorter even when applied on a basic substrate or a low reflectance substrate and which comprises an acid generator comprising an aliphatic sulfonium salt represented by the following formula (I):

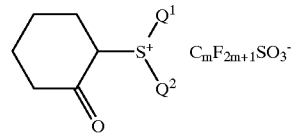

(I)

wherein $Q^1$ represents an alkyl group, $Q^2$ represents an alkyl or a residue of an alicyclic hydrocarbon and m represents an integer of 1 to 8; and onium salt selected from triphenylsulfonium salts represented by the following formula (IIa) and diphenyliodonium salts represented by the following formula (IIb):

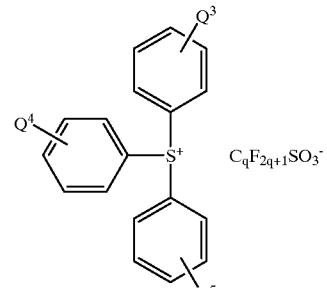

(IIa)

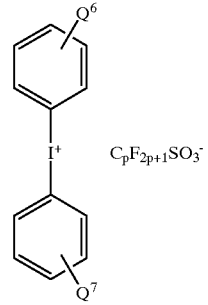

(IIb)

wherein $Q^3$, $Q^4$, $Q^5$, $Q^6$ and $Q^7$ each independently represent a hydrogen atom, a hydroxyl group, an alkyl group having 1 to 6 carbon atoms, an alkoxy group having 1 to 6 carbon atoms, and q and p represent a integer of 4 to 8; and (2) a resin which has a polymerization unit with a group unstable to an acid, and is insoluble or barely soluble in alkali by itself but changes soluble in alkali by an action of the acid, is provided.

16 Claims, No Drawings

CHEMICAL AMPLIFICATION TYPE POSITIVE RESIST

BACKGROUND OF THE INVENTION

The present invention relates to a chemical amplification type positive resist.

The fine processing in the production of semiconductor has usually been performed by adopting the lithography process using a resist composition. In the lithography process, principally, resolution can be improved by shortening wavelength for exposure, as indicated by the Rayleigh's equation for limit of diffraction. Accordingly, wavelength of the light source for lithography process used in the production of semiconductors has become shorter and shorter in such order as g-ray at a wavelength of 436 nm, i-ray at a wavelength of 365 nm. KrF excimer laser at a wavelength of 248 nm. ArF eximer laser at a wavelength of 193 nm is expected as a next generation light source, and some kinds of resists for ArF eximer laser is now being put to practical use.

Since lenses in exposing machines using ArF excimer laser have a shorter lifetime as compared with the lenses for the conventional exposing light source, the shorter time for exposing such lenses to ArF excimer laser ray is preferred. In order to make the exposure time shorter, sensitivity of the resists is to be increased, and for such purpose, so called chemical amplification type resists are used. The chemical amplification type resist contains a resin having a group cleavable by the action of an acid. and utilizes a catalytic action of the acid generated by exposure to the ray.

It has been known that resins used in resists to be exposed to ArF excimer laser preferably have no aromatic ring in order to insure the transmittance of the resists and have an alicyclic ring in place of an aromatic ring in order to confer a dry etching resistance. Various resins have been known as resins meeting such requirements. For example, D. C. Hofer, J. Photopolym. Sci. Technol., Vol. 9. No. 3, pages 387–398 (1996) describes such resins.

S. Takeuchi et al., J. Photopolym. Sci. Technol., Vol. 9, No. 3, pages 475–487 (1996) and JP-A-9-73173 also describe that, when polymers or copolymers of 2-methyl-2-adamantyl methacrylate are used as resins for chemical amplification type resist, a positive working action is realized by cleavage of 2-methyl-2-adamantyl group by the action of an acid and a high dry etching resistance, high resolution and a good adherence to substrate are obtained. JP-A-10-274852 also describes that the adherence to substrate is Improved by using a resin having a butyrolactone residue in a part of polymerization units, as a resin composing a chemical amplification type positive resist composition. In addition, JP-A-10-319595 describes a positive resist composition using a resin having a carboxyl group protected by γ-butyrolactone-3-yl residue.

On the other hand, since the chemical amplification type resists utilizes the action of an acid, the profiles are liable to be bottom-tailed by deactivation of the acid when the substrate is of a basic nature. It is known that this problem can be resolved by adding a much amount of a basic quencher substance. Addition of a much amount of such quencher substance, however, results in decrease of the sensitivity. When ArF eximer laser is used as the light for exposure, the resist is often applied on a substrate having a low reflection, such as an organic or inorganic anti-reflection film. When such a substrate having a low reflection is used, the profile of the resist generally deteriorated to a taper shape, although dimension uniformity is effectively improved.

It is contemplated that a reduced quantity of an acid generator in a resist composition In order to lessen light absorption, but in this case, a sensitivity generally decreases. As other methods to lessen light absorption, the use of aliphatic sulfonium salts having a high transparency is contemplated, as described in JP-A-7-25846, JP-A-7-28237, JP-A-7-92675 and JP-A-8-27102. With such well-known aliphatic sulfonium salts, however, no sufficient resolution is achieved. In addition the problem of bottom-tailed profile on a substrate of a basic nature is not solved either. In such a way, a chemical amplification type resist using a conventional acid generator has had the problem that its performance, in particular a resist pattern profile, are varied depending on the kinds of the substrate.

An object of the present invention is to provide a chemical amplification type positive resist composition, containing a resin component and an acid generator, suitable for the ArF or KrF excimer laser lithography and the like, particularly lithography using a light of a wavelength of 220 nm or shorter such as the ArF excimer laser lithography, and not only excellent in resist performances such as sensitivity, resolution and adhesion to a substrate, but producing a good pattern profile on any kind of substrate with a little dependence on kinds of substrate, even being used with a basic substrate and a low reflectance substrate.

Another object of the present invention is to provide a compound useful as an acid generator for the chemical amplification type positive resist composition.

The present inventors has found that resolution of a chemical amplification type positive resist composition is improved and further, a pattern profile thereof is also improved even on a basic substrate and a low reflectance substrate, when certain kinds of acid generators are in combination or an acid generator of a specific structure selected from the certain kinds are used. Thus, the present invention has been completed.

SUMMARY OF THE INVENTION

The present invention provides a chemical amplification type positive resist composition (hereinafter referred to as composition A) which comprises (1) an acid generator comprising
an aliphatic sulfonium salt represented by the following formula (I):

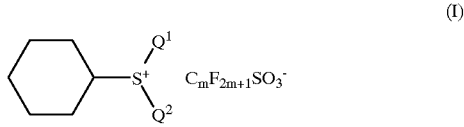

wherein $Q^1$ represents an alkyl group, $Q^2$ represents an alkyl or a residue of an alicyclic hydrocarbon and m represents an integer of 1 to 8; and at least one onium salt selected from triphenylsulfonium salts represented by the following formula (IIa) and diphenyiodonium salts represented by the following formula (IIb):

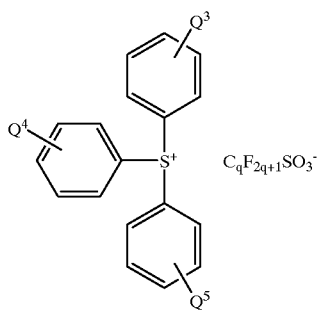

(IIa)

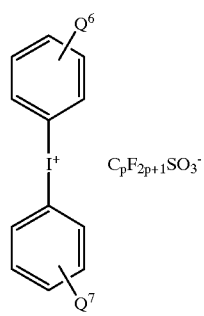

(IIb)

wherein $Q^3$, $Q^4$, $Q^5$, $Q^6$ and $Q^7$ each independently represent a hydrogen atom, a hydroxyl group, an alkyl group having 1 to 6 carbon atoms, an alkoxy group having 1 to 6 carbon atoms, and q and p represent a integer of 4 to 8; and (2) a resin which has a polymerization unit with a group unstable to an acid, and is insoluble or barely soluble in alkali by itself but changes soluble in alkali by an action of the acid.

Aliphatic sulfonium salts represented by the formula (I) wherein m is in the range of 4 to 8 are conspicuous in effects to improve a resolution and a pattern profile and furthermore, impart an excellent resolution and a good pattern profile even when the onium salt selected from triphenylsulfonium salts and diphenyiodonium salts represented by the formulae (IIa) and (IIb), respectively.

Therefore, the present invention provides a chemical amplification type positive resist composition (hereinafter referred to as composition B) which comprises (1) an acid generator comprising
an aliphatic sulfonium salt represented by the following formula (Ia):

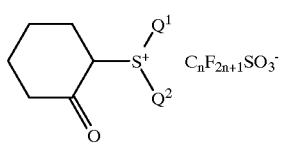

(Ia)

wherein $Q^1$ and $Q^2$ are as defined above and n represents an integer of 4 to 8; and (2) a resin which has a polymeriation unit with a group unstable to an acid, and is insoluble or barely soluble in alkali by itself but changes soluble in alkali by an action of the acid.

It is more effective to use an aliphatic sulfonium salt represented by the formula (Ia) and at least one onium salt selected from triphenylsulfonium salts and diphenyiodonium salts represented by the formulae (IIa) and (IIb), respectively, in combination.

The present Invention further provides a sulfonium salt represented by the formula (Ia).

PREFERRED EMBODIMENT OF THE INVENTION

An acid generator used in a chemical amplification type resist composition decomposes to generate an acid under radiation such as light or an electron beam to the acid generator itself or a resist composition including the acid generator. In the composition (A) of the present invention, as acid generators, an aliphatic sulfonium salt represented by the formula (I), and at least one onium salt selected from triphenylsulfonium salts represented by the formula (IXa) and diphenyliodonium salts represented by the formula (IIb) are used in combination. Further, in the composition (B), as an acid generator, an aliphatic sulfonium salt represented by the formula (I), wherein m is in the range of 4 to 8, that is, an aliphatic sulfonium salt represented by the formula (Ia), is used.

In the formulae (I) and (Ia), $Q^1$ represents an alkyl group and $Q^2$ represents an alkyl group or a residue of an alicyclic hydrocarbon. The alkyl group generally has about 1 to 8 carbon atoms. When the number of carbon atoms is 3 or more, the alkyl group may be either a straight chain or a branched chain. Examples of the alkyl group include methyl, ethyl, propyl, isopropyl, butyl, tert-butyl, pentyl and hexyl. The residue of alicyclic hydrocarbon represented by $Q^2$ generally has about 5 to 16 carbon atoms. Examples of the residue of alicyclic hydrocarbon represented by $Q^2$ include monocycloalkyl groups such as cyclopentyl, cyclohexyl and cyclooctyl and crosslinked polycyclic groups such as norbornyl, isobornyl and adamantyl. Further, m, representing the number of carbon atoms in an alkane portion constituting perfluoroalkanesulfonate anion in the formula (I), is an integer of 1 to 8. Examples of the perfluoroalkanesulfonate anion in the formula (I) include trifluoromethane sulfonate ion, perfluorobutanesufonate ion and perfluorooctanesulfonate ion.

An aliphatic sulfonium s t represented by the formula (I) has a high transmittance for light of 220 nm or shorter in wavelength, for example ArF excimer laser light of 193 nm in a wavelength. Therefore, a resist composition comprising such an aliphatic sulfonium salt as an acid generator is less absorptive to exposure light of the short wavelength as described above and a taper shaped profile is prevented.

However, when an aliphatic sulfonium salt represented by the formula (I) wherein the number of carbon atoms in a portion of perfluoroalkanesulfonate anion is small, for example, in a case of trifluoromethane sulfonate anion, is singly used as the acid generator, not only is a sufficient resolution hard to be attained, but a good pattern profile is also hard to be achieved especially on a basic substrate. When an aliphatic sulfonium salt of the formula (I) and at least one onium salt selected from compounds represented by the formulae (IIa) or (IIb) are used as the acid generator in combination, resolution can be raised with no degradation in substrate dependence as compared with the case wherein the aliphatic sulfonium salt is singly used as the acid generator, and furthermore, sensitivity can also be improved with no degradation in substrate dependence as compared with the case wherein the the onium salt selected from compounds of the formulae (IIa) or (IIb) is singly used.

Even when the aliphatic sulfonium salt of the formula (I) is singly used as an acid generator, if m is 4 or more in the formula (I), a good resolution and a good pattern profile on a basic substrate or a low reflectance substrate can be obtained. In a resist composition (B), a compound of the formula (I) in which m is 4 or more, that is, aliphatic sulfonium salts represented by the formlula (Ia) is used as the acid generator.

Aliphatic sulfonium salts represented by the formula (I) can be obtained as a commodity on the market. Further, the salts of the formula (I) can be produced according to a known process as well. For example, an aliphatic sulfonium salt can be produced according to the following reaction scheme, which is an application of the process described in D. N. Kevill et al., J. Am. Chem. Soc., Vol. 108. 1579–1585 (1986).

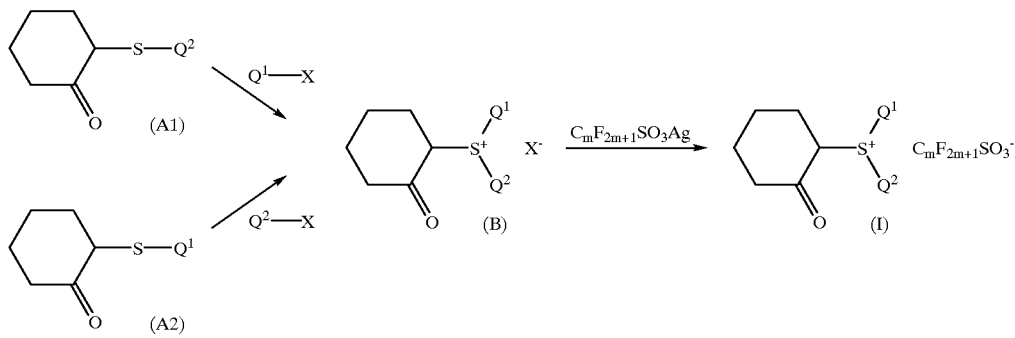

wherein $Q^1$, $Q^2$ and m are as defined above and X represents a halogen atom such as bromine or iodine.

That is, a halogenated hydrocarbon of the formula $Q^1$—X is reacted with a sulfide compound of the formula (A1) or alternatively, a halogenated hydrocarbon of the formula $Q^2$—X is reacted with a sulfide compound of the formula (A2) and thereby, a sulfonium halide represented by the formula (B) is produced. Then, silver perfluoroalkanesulfonate of the formula $C_mF_{2m+1}SO_3Ag$ is reacted with thus produced sulfonium halide and thereby an aliphatic sulfonium salt represented by the formula (I) or (Ia) is obtained. The reactions are carried out in a proper solvent, such as acetonitrile, nitromethane or ethyl acetate. The halogenated hydrocarbon of the formula $Q^1$—X or $Q^2$—X is preferably used in excess, for example in amount of about 3 to 20 times in mol ratio, relative to a sulfide compound of the formula (A1) or (A2) while the silver perfluoroalkanesulfonate of the formula $C_mF_{2m+1}SO_3Ag$ may be used in almost equi-molar ratio to the sulfide compound of the formula (A1) or (A2). After the reaction, generated silver halide is removed by filtration or the like and the filtrate is then subjected to after-treatments such as concentration or recrystallization and thereby the aliphatic sulfonium salt of the formula (I) or (Ia) can be obtained.

Examples of aliphatic-sulfonium salts represented by the formula (I) include the following compounds, and among them, the compounds in which m is 4 to 8 are also ones represented by the formula (Ia):

cyclohexylmethyl(2-oxocyclohexyl)sulfonium trifluoromethanesulfonate, which is a compound represented by the formula (I), wherein $Q^1$=methyl, $Q^2$=cyclohexyl and m=1, 1-adamantylmethyl(2-oxocyclohexyl)sulfonium trifluoromethanesufonate, which is a compound represented by the formula (I), wherein $Q^1$=methyl, $Q^2$=1-adamantyl and m=1, methyl(2-norbornyl)(2-oxocyclohexyl)sulfonium trifluoromethanesufonate, which is a compound represented by the formula (I), wherein $Q^1$=methyl, $Q^2$=2-norbornyl and m=1, dimethyl(2-oxocyclohexyl)sulfonium trifluoromethanesufonate, which is a compound represented by the formula (I), wherein $Q^1$ and $Q^2$=methyl and m=1, methyl(2-oxocyclohexyl)propylsulfonium trifluoromethanesufonate which is a compound represented by the formula (I), wherein $Q^1$=propyl, $Q^2$=methyl and m=1, cyclohexylmethyl(2-oxocyclohexyl)sulfonium perfluorobutanesufonate, which is a compound represented by the formula (I), wherein $Q^1$=methyl, $Q^2$=cyclohexyl and m=4, 1-adamantylmethyl(2-oxocyclohexyl)sulfonium perfluorobutanesufonate, which is a compound represented by the formula (I), wherein $Q^1$=methyl, $Q^2$=1-adamantyl and m=4, methyl(2-norbonyl)(2-oxocyclohexyl)sulfonium perfluorobutanesufonate, which is a compound represented by the formula (I), wherein $Q^1$=methyl, $Q^2$=2-norbonyl and m=4, dlmethyl(2-oxocyclohexyl)sulfonium perfluorobutanesufonate, which is a compound represented by the formula (I), wherein $Q^1$ and $Q^2$ methyl and m=4, methyl(2-oxocyclohexyl)propylsulfonium perfluorobutanesufonate, which is a compound represented by the formula (I), wherein $Q^1$=propyl, $Q^2$ methyl and m=4, cyclohexylmethyl(2-oxocyclohexyl)sulfonium perfluorooctanesufonate, which is a compound represented by the formula (I), wherein $Q^1$=methyl, $Q^2$=cyclohexyl and m=8, 1-adamantylmethyl(2-oxocyclohexyl)sulfonium perfluorooctanesufonate, which is a compound represented by the formula (I), wherein $Q^1$=methyl, $Q^2$=1-adamantyl and m=8, methyl(2-norbornyl)(2-oxocyclohexyl)sulfonium perfluorooctanesufonate, which is a compound represented by the formula (I), wherein $Q^1$=methyl, $Q^2$=2-norbornyl and m=8, dimethyl (2-oxocyclohexyl )sulfonium perfluorooctanesufonate, which is a compound represented by the formula (I), wherein $Q^1$ and $Q^2$=methyl and m=8, and methyl(2-oxocyclohexyl)propylsulfonium perfluorooctanesufonate, which is a compound represented by the formula (I), wherein $Q^1$=propyl, $Q^2$=methyl and m=8.

In the formulae (IIa) and (IIb), $Q^3$, $Q^4$, $Q^5$, $Q^6$ and $Q^7$, which are same to or different from each other, are a hydrogen atom, a hydroxyl group, an alkyl group having 1 to 6 carbon atoms or an alkoxy group having 1 to 6 carbon atoms. The alkyl group and the alkoxy group in which the number of carbon atoms is 3 or more may be of a straight chain or branched chain. Examples of alkyl groups represented by $Q^3$, $Q^4$, $Q^5$, $Q^6$ and $Q^7$ include methyl, ethyl, propyl, isopropyl, butyl, tert-butyl, pentyl and hexyl. Examples of alkoxy groups include methoxy, ethoxy, propoxy and butoxy. Further, in the formulae (IIa) and (IIb), o and q, which are are same to or different from each other and representing the number of carbon atoms in an alkane portion constituting perfluoroalkanesulfonate anion, are an Integer in the range of 4 to 8. A triphenylsufonium salt having a perfluoroalkanesulfonate anion having 4 to 8 carbon atoms is advantageous in improvement of resolution and improvement of a pattern profile on a basic substrate or a low reflectance substrate.

Triphenylsulfonium salts represented by the formula (IIa) and diphenyliodonium represented by the formula (IIb) can be commodities on the market. Alternatively, those can be produced according to an ordinary process. For example, the triphenylsulfonium salt (IIa) can be produced according to one of the following processes: a process in which a corresponding triphenylsulfonium bromide is reacted with Ag perfluoroalkanesulfonate; a process in which, a corresponding diphenylsulfoxide, a benzene compound and a perfluoroalkanesulfonic acid are reacted in the presence of trifluoroacetic anhydride, according to the description in Chem. Pharm. Bull., Vol. 29, 3753 (1981); and a process in which a corresponding aryl Grignard reagent is reacted with thyonyl chloride, the resultant product is further reacted with a triorganosilyl halide to form a triarylsulf onium halide and thereafter, the triarylsulfonium halide is further reacted with silver perfluoroalkanesulfonate, according to the description of JP-A-8-311018. Compounds represented by the formula (IIa) wherein $Q^3$, $Q^4$ and/or $Q^5$ is a hydroxyl group can be produced in a process in which, according to the description in JP-A-8-311018, a triphenylsulfonium salt having a tert-butoxy group on a benzene ring is treated with a sulfonic acid and thereby, a tert-butyl group is eliminated to obtain a target compound.

Further, a diphenyliodonium salt represented by the formula (IIb) can be produced, for example, by a process in which iodyl sulfate and a corresponding aryl compound are reacted with each other and thereafter, a perfluoroalkanesulfonic acid is added to the resultant product, according to the description in J. Am. Chem. Soc., Vol. 81, 342 (1959); a process in which concentrated sulfuric acid is added dropwise to a mixture of a corresponding aryl compound, acetic anhydride and potassium iodate to cause a reaction and thereafter, a perfluoroalkanesulfonic acid is added to the resultant product; or a process in which iodine and trifluoroacetic acid are added to a mixture of acetic anhydride and fuming nitric acid, then, a corresponding aryl compound is reacted with the resultant product and, thereafter, a perfluoroalkanesulfonic acid is further added thereto.

Examples of triphenylsulfonium salts and diphenyliodonium represented by the formulae (IIa) and (IIb), respectively, include the following compounds:

triphenylsulfonium perfluorobutanesulfonate, 4-methylphenyldiphenylsulfonium perfluorobutanesulfonate, 4-hydroxyphenyldiphenylsulfonium perfluorobutanesulfonate, 4-methoxyphenyldiphenylsulfonium perfluorobutanesulfonate, tris(4-methyldiphenyl)sulfonium perfluorobutanesulfonate, tris(4-methoxyphenyl)sulfonium perfluorobutanesulfonate, and triphenylsulfonium perfluorooctanesulfonate, 4-methylphenyldiphenylsulfonium perfluorooctanesulfonate, 4-hydroxyphenyldiphenylsulfonium perfluorooctanesulfonate, 4-methoxyphenyldiphenylsulfonium perfluorooctanesulfonate, tris (4-methylphenyl)sulfonium perfluorooctanesulfonate, tris (4-methoxyphenyl)sulfonium perfluorooctanesulfonate, diphenyliodonlum perfluorobutanesulfonate, di(4-methoxyphenyl) iodonium perfluorooctanesulfonate, and di(4-tert-butylphenyl) iodonium perfluorooctanesulfonate.

The resin comprised in the resist composition of the present invention have a polymerization unit with a group unstable to an acid. Resins used in chemical amplification type positive resists are generally insoluble or barely soluble in alkali before the exposure to light in the lithography process, and it becomes soluble in alkali after cleavage of a part of the groups by the action of an acid. The group unstable to an acid in the resin used in the present invention may be one of various groups which have been known as such groups.

As examples of such group unstable to an acid, various kinds of carboxylic acid esters can be mentioned. Examples of the carboxylic acid esters include alkyl esters such as methyl ester and tert-butyl ester, acetal type esters such as methoxymethyl ester, ethoxymethyl ester, 1-ethoxyethyl ester, 1-isobutoxyethylester, 1-isopropoxyethylester, 1-ethoxypropyl ester, 1-(2-methoxyethoxy)ethyl ester, 1-(2-acetoxyethoxy)ethyl ester, 1-[2-(1-adamantyloxy)ethoxy] ethyl ester, 1-[2-(1-adamantylcarbonyloxy)ethoxy]ethyl ester, tetrahydro-2-furyl ester and tetrahydro-2-pyranyl ester, and alicyclic esters such as isobornyl ester and 2-alkyl-2-adamantyl ester. Monomers used for introducing the polymerization units with a carboxylate ester in the resin may be (meth)acrylic monomers such as methacrylic ester and acrylic ester, or alicyclic monomers with a carboxylic ester bound thereto such as norbornenecarboxylic ester, tricyclodecenecarboxylic ester and tetracyclodecenecarboxylic ester.

Among resins of the present invention, a resin having a polymerization unit of 2-alkyl-2-adamantyl (meth)acrylate is preferable since it imparts a resist including the resin excellent resolution. This polymeric unit is formed by cleavage of a double bond of a (meth)acrylic acid portion in 2-alkyl-2-adamantyl acrylate or 2-alkyl-2-adamantyl methacrylate, and the polymerization unit can be represented by the following formula (III):

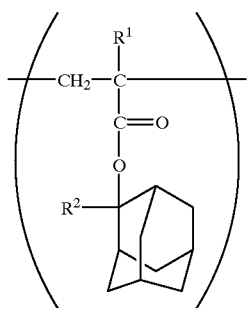

(III)

wherein R¹ represents a hydrogen atom or a methyl group and R² an alkyl group.

The polymerization unit 2-alkyl-2-adamantyl (meth)acrylate represented by the formula (III) contributes to the transmittance of the resist and improvement of dry etching resistance due to the presence of the adanantane nucleus which is an alicyclic ring. Since the 2-alkyl-2-adamnatyl group in this unit is cleaved by the action of an acid, the unit contributes to enhance solubility in alkali after exposure of the resist film The group R² in the formula (III) is an alkyl group. This alkyl usually have about 1 to 8 carbon atoms Preferably, it is a linear chain in usual case but may be branched when it has 3 or more carbon atoms. Examples of R² include methyl, ethyl, propyl, isopropyl and butyl. Amongst them, methyl or ethyl is preferred as R²for improvement of adhesiveness to substrate and resolution.

Examples of monomers used for introducing the 2-alkyl-2-adamantyl (meth)acrylate polymerization unit represented by the formula (III) in the resin include 2-methyl-2-adamnatyl acrylate, 2-ethyl-2-adamnatyl acrylate, 2-methyl-2-adamnatyl methacrylate and 2-ethyl-2-adamnatyl methacrylate. 2-Alkyl-2-adamantyl (meth)acrylates can be produced, for example, by the reaction of a 2-alkyl-2-adamantanol or a metal salt thereof with an acryloyl halide or a methacryloyl halide.

Resins comprised in the resist composition of the present invention may also have other polymerization units that are not cleaved or hard to be cleaved by an action of an acid, in addition to the polymerization units with a group unstable to an acid. As the other polymerization units, for example, polymerization units introduced from a free carboxylic group such as acrylic acid or methacrylic acid, polymerization units introduced from an aliphatic unsaturated dicarboxylic anhydride such as maleic anhydride and itaconic anhydride, a polymerization unit introduced from 2-norbornene, a polymerization unit introduced from (meth)acrylonitrile, and polymerization units introduced from (meth)acrylic esters such as 2-hydroxyethyl (meth)acrylate, 3-hydroxy-1-adamantyl (meth)acrylate, and (meth)acryloyloxy-γ-butyrolactone can be mentioned.

Particularly, a polymerization unit introduced from 3-hydroxy-1-adamantyl (meth)acrylate and a polymerization unit introduced from (meth)acryloyloxy-γ-butyrolactone, wherein the lactone ring may be optionally substituted with an alkyl group, are preferred, since they provide a resist with excellent adhesion to a substrate. The term a polymerization unit introduced from 3-hydroxy-1-adamantyl (meth)acrylate means a unit formed by cleavage of a double bond of a (meth)acrylic acid portion in corresponding 3-hydroxy-1-adamantyl (meth)acrylate, which unit is represented by the formula (IV) mentioned below. Further, the term a polymerization unit introduced from (meth)acryloyloxy-γ-butyrolactone, wherein the lactone ring may be optionally substituted with an alkyl group, means a unit formed by cleavage of a double bond of a (meth)acrylic acid portion in α-(meth)acryloyoxy-γ-butyrolactone wherein the lactone ring is unsubstituted or substituted with an alkyl group, or alternatively, a unit formed by cleavage of a double bond of a (meth)acrylic acid portion in β-(meth)acryloyoxy-γ-butyrolactone wherein the lactone ring is unsubstituted or substituted with an alkyl group, and the polymeric units are represented by the following formulae (V), (VI), respectively.

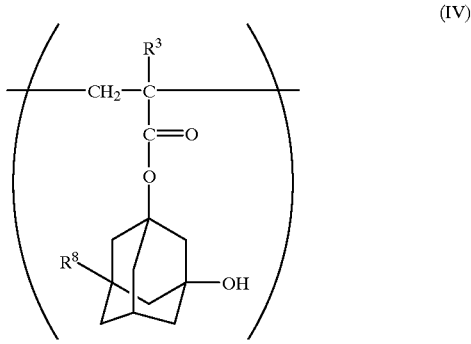

(IV)

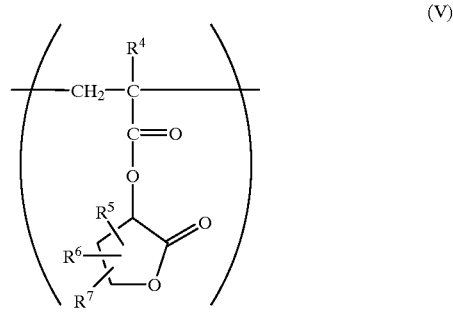

(V)

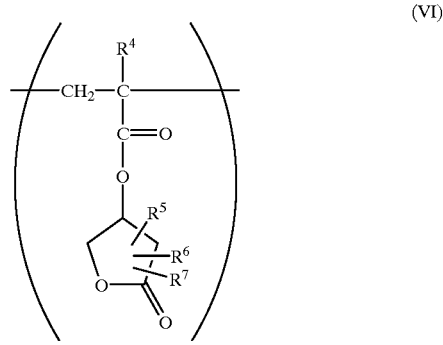

(VI)

wherein R³ and R⁴ each independently represent a hydrogen atom or a methyl group, R⁵, R⁶ and R⁷ each independently represent a hydrogen atom or an alkyl group and R⁶ represents a hydrogen atom or a hydroxyl group.

3-Hydroxy-1-adamantyl (meth)acrylates used for introducing to the unit of the formula (IV) are available on the market. Alternatively, it can also be produced, for example, by reacting a corresponding hydroxyadamantane with (meth)acrylic acid or a halide of the acid. Further, α- or β-(meth)acryloyloxy-γ-butyrolactone used for introducing to the unit of the formula (V) or (VI), respectively, can be produced by reacting acrylic acid or methacrylic acid with α- or β-bromo-γ-butyrolactone, wherein the lactone ring may be optionally substituted with an alkyl group, or alternatively by reacting acrylic halide or methacrylic halide with α- or β-hydroxy-γ-butyrolactone, wherein the lactone ring may be optionally substituted with an alkyl group.

A polymerization unit of 3-hydroxy-1-adamantyl (meth)acrylate represented by the formula (IV), a polymerization unit of α-(meth)acryloyloxy-γ-butyrolactone represented by the formula (V) and a polymerization unit of β-(meth)acryloyloxy-γ-butyrolactone represented by the formula (VI)have high polarities and adhesion of a resist containing any of the polymerization units to a substrate is improved Further, the polymerization units contribute to higher resolution of a resist as well. Still further, the polymerization unit of 3-hydroxy-1-adamantyl (meth)acrylates also contributes to excellent dry etch resistance of a resist. Further, the polymerization unit of β-(meth)acryloyloxy-γ-butyrolactone contributes to improvement of transmittance of a resist.

Examples of monomers used for introducing the polymerization unit represented by the formula (IV) include 3-hydroxy-1-adamantyl acrylate, 3-hydroxy-1-adamantyl methacrylate, 3,5-dihydroxy-1-adamantyl acrylate and 3,5-dihydroxy-1-adamantyl methacrylate. $R^5$, $R^6$ and $R^7$ in the formulae (V) and (VI) each independently represent a hydrogen atom or an alkyl group. The alkyl groups represented by $R^5$, $R^6$ or $R^7$ generally have 1–6 carbon atoms. When the number of carbon atoms is 3 or more, the alkyl groups may be a straight chain or branched chain. Examples of the alkyl groups represented by $R^5$, $R^6$ or $R^7$ include methyl, ethyl, propyl and butyl. Examples of monomers used for introducing the polymerization unit represented by the formula (V) include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, and α-methacryloyloxy-α-methyl-γ-butyrolactone. Examples of monomers used for introducing the polymerization unit represented by the formula (VI) include β-acryloyloxy-γ-butyrolactone, β-methacryloyloxy-γ-butyrolactone, and β-methacryloyloxy-α-methyl-γ-butyrolactone.

A resin comprised in the resist composition of the present invention can further have a polymerization unit introduced from 2-norbornene. A resin with a polymerization unit introduced from 2-norbornene imparts good in dry etch resistance to the resist comprising it. A polymerization unit introduce form 2-norbornene can be introduced into a main chain by radical polymerization in which, for example, a corresponding 2-norbonene, an aliphatic unsaturated dicarboxylic anhydride such as maleic anhydride or itaconic anhydride and the above described other monomers are copolymerized. Therefore, the polymerization unit introduced from 2-norbornene is formed by cleavage of a double bond of 2-norbornene, and can be represented by the formula (VII) mentioned below. Polymerization units introduced from maleic anhydride and itaconic anhydride, which are ones of aliphatic unsaturated dicarboxylic anhydrides, are formed by cleavage of a double bond of each of them and can be represented by the following formulae (VIII) and (IX), respectively.

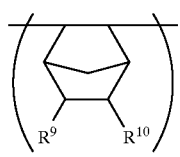

(VII)

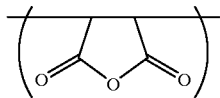

(VIII)

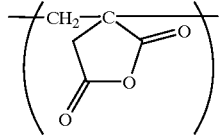

(IX)

In the formula (VII), $R^9$ and $R^{10}$ each independently represent a hydrogen, an alkyl group having 1–3 carbon atoms, a hydroxyalkyl group having 1–3 carbon atoms, a carboxyl group, a cyano group or a —COOZ group in which Z represent a residue of an alcohol; or alternatively $R^9$ and $R^{10}$ can form a residue of a carboxylic anhydride represented by —C(=O)OC(=O)— in combination. Examples of alkyl groups represented by $R^9$ or $R^{10}$ include methyl, ethyl and propyl. Examples of hydroxyalkyl represented by $R^9$ and $R^{10}$ include hydroxymethyl and 2-hydroxyethyl. Examples of the residues of alcohol represented by Z include alkyl groups having about 1–8 carbon atoms, which may be optionally substituted, and 2-oxooxolane-3- or -4-yl. Examples of the substituents on the alkyl groups include a hydroxyl group and a residue of alicyclic hydrocarbon. Examples of a residue of a carboxylic esters represented by —COOZ include methoxycarbonyl, ethoxycarbonyl, 2-hydroxyethoxycarbonyl, tert-butoxycarbonyl, 2-oxooxolane-3-yloxycarbonyl, 2-oxooxolane-4-yloxycarbonyl, 1,1,2-trimethylpropoxycarbonyl, 1-cyclohexyl-1-methylethoxycarbonyl, 1-(4-methylcyclohexyl)-1-methylethoxycarbonyl and 1-(1-adamantyl)-1-methylethoxycarbonyl.

Examples of monomers used for introducing a polymerization unit of 2-norbornen represented by the formula (VI) include the following compounds:

2-norbornene, 2-hydroxy-5-norbornene, 5-norbornene -2-carboxylic acid, methyl 5-norbornene-2-carboxylate, t-butyl 5-norbornene-2-carboxylate, 1-cyclohexyl-1-methylethyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl)ethyl 5-norbornene-2-carboxylate, 1-(1-adamantyl)-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 2-hydroxy-1-ethyl 5-norbornene-2-carboxylate, 5-norbornene-2-methanol, and 5-norbornene-2,3-dicarboxylic anhydride.

Although the preferable ratio of a polymerization unit with a group unstable to an acid in the resin comprised in the resist composition of the present invention, based on all polymerization units of the resin varies according to a kind of radiation for patterning exposure and a kind of an acid, it is generally in the range of 10 to 80 mol %. In particular, a preferable ratio of a polymerization unit introduced from 2-alkyl-2-adamantyl (meth)acrylate represented by the formula (III) based on all the polymerization units of the resin is in the range of 15 to 80 mol %. Further, when, in addition to a polymerization unit with a group unstable to an acid, other polymerization units hard to be cleaved by an action of an acid are present in a resin, such as a polymerization unit represented by the formula (IV), introduced from 3-hydroxy-1-adamantyl (meth)acrylate, a polymerization unit represented by the formula (V), introduced from α-(meth)acryloyloxy-γ-butyrolactone, a polymerization unit represented by the formula (VI), introduced from β-(meth) acryloyloxy-γ-butyrolactone, a polymerization unit represented by the formula (VII), introduced from 2-norbornene, a polymerization unit represented by the formula (VIII), introduced from maleic anhydride, and a polymerization unit represented by the formula (IX), introduced from itaconic anhydride, the ratio of the sum of the other polymerization units based on all the polymerization units of the resin is preferably in the range of 20 to 90 mol %.

Therefore, in the production of a copolymer having a polymerization unit represented by the formula (IV) and/or a polymerization unit represented by the formula (V) and a polymerization unit represented by the formula (VII), and a polymerization unit represented by the formula (VIII) and/or a polymerization unit represented by the formula (IX) in addition to a polymerization unit with a group unstable to an acid, including a polymerization unit represented by the formula (III), preferably, a monomer mixture composed of a monomer having a group unstable to an acid, including 2-alkyl-2-adamantyl (meth)acrylate, and 3-hydroxy-1-adamantyl (meth)acrylate, α-(meth)acryloyloxy-γ-butyrolactone wherein the lactone ring may be optionally substituted with an alkyl group, 2-norbornene, and a maleic anhydride and/or itaconic anhydride is subjected to a copolymerization, wherein the ratio of a monomer having a group unstable to an acid based on the all the monomers is 10 to 80 mol %, particularly the ratio of 2-alkyl-2-adamantyl (meth)acrylate is 15 to 80 mol %, and the ratio of the total of 3-hydroxy-1-adamantyl (meth)acrylate, α-(meth) acryloyloxy-γ-butyrolactone wherein the lactone ring may be optionally substituted with an alkyl group, 2-norbornene, maleic anhydride and itaconic anhydride based on the all the monomers is 20 to 90 mol %.

When 2-norbornenes and aliphatic unsaturated dicarboxylic anhydride, such as maleic anhydride and itaconic anhydride, are used for the copolymerization, the compounds are preferably used in excess since their polymerization activities are relatively little.

Similarly, in the production of a copolymer having a polymerization unit represented by the formula (VI) in addition to the above-mentioned other polymerization units, preferably, a monomer having a group unstable to an acid, including 2-alkyl-2-adamantyl (meth)acrylate, and a monomer mixture containing β-(meth)acryloyloxy-γ-butyrolactone wherein the lactone ring may be optionally substituted with an alkyl group are subjected to a copolymerization, wherein the ratio of the monomer having a group unstable to an acid based on the all the monomers used is 10 to 80 mol %, and the ratio of the monomer mixture containing β-(meth)acryloyloxy-γ-butyrolactone wherein the lactone ring may be optionally substituted with an alkyl group based on the all the monomers is 20 to 90 mol %.

It has been known that, generally, in the composition of chemical amplification type positive resist, deterioration of performance due to deactivation of an acid by standing after exposure can be improved by adding a basic compound, particularly a basic nitrogen-containing organic compound such as an amine compound, as a quencher. Likewise, in the present invention, addition of such a basic compound is preferred. Specific examples of the basic compounds used as quenchers include the compounds represented by the following formulae:

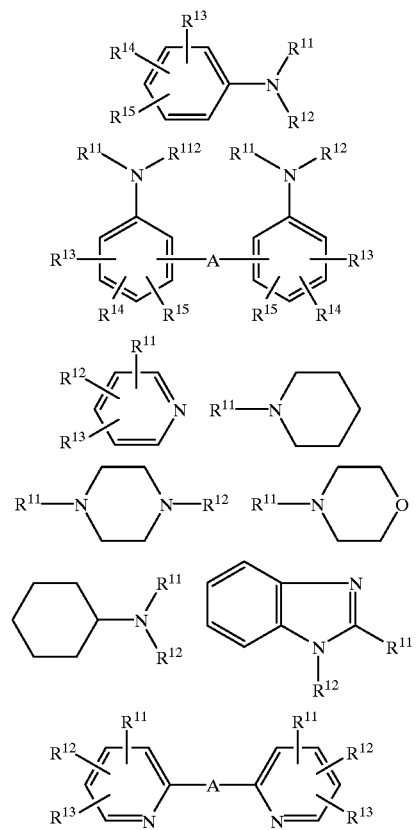

wherein $R^{11}$, $R^{12}$, $R^{13}$, $R^{14}$ and $R^{15}$ independently represent hydrogen, alkyl which may be substituted with a hydroxyl group, cycloalkyl, aryl or alkoxy, and A represents alklene, carbonyl or imino. The alkyl and alkoxy represented by $R^{11}$, $R^{12}$, $R^{13}$, $R^{14}$ and $R^{15}$ usually have about 1 to 6 carbon atoms, cycloalkyl usually have about 5 to 10 carbon atoms and aryl usually have about 6 to 10 carbon atoms. The alkylene represented by A usually have about 1 to 6 carbon atoms and may be a linear chain or a branched chain.

A 2,6-dialkylpyridine compound represented by the following formula (X):

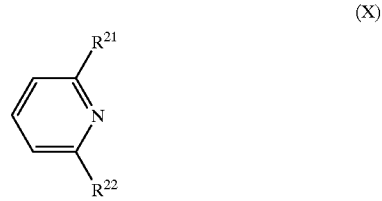

(X)

wherein $R^{21}$ and $R^{22}$ independently represent an alkyl group having 1 to 4 carbon atoms, is especially effective for improvement of storage stability of a resist among basic compounds used as a quencher. Examples of the 2,6- dialkylpyridine compound include 2,6-lutidine, 2-ethyl-6-methylpyridine, and 2,6,-di-tert-butylpyridine. The 2,6-dialkylpyridine compound can be used as a quencher singly or in combination with other basic compounds, as desired.

The resist composition of the invention preferably comprises the resin in a range of about 80 to 99.9% by weight and the acid generator in a range of about 0.1 to 20% by weight, based on the total solid content.

In the composition A of the present invention, the weight ratio of the aliphatic sulfonium salt represented by the formula (I) to the onium salt selected from triphenylsulfonium salts represented by the formula (IIa) and diphenyiodonium salts represented by the formula (IIb) is about 9:1 to 1:9, preferably 8:2 to 2:8.

In the composition B of the present invention, the weight ratio is preferably about 9:1 to 1:9 and more preferably in the ange of 8:2 to 2:8.

When a basic compound as a quencher is used, preferably it is contained in a range of about 0.0001 to 0.1% by weight, based on the total solid content. In addition, the resist composition of the present invention may contain, if necessary, various additives such as photo-sensitizer, dissolution inhibitor, other resin, surfactant, stabilizer and dye.

The resist composition of the invention is usually used as a resist solution in which the above described components are dissolved in a solvent and the resist solution applied onto a substrate such as a silicone wafer according to a conventional method, such as spin coating. The solvent usable here may be anyone insofar as it dissolve the components, has a suitable drying rate and gives a uniform and smooth film after evaporation of the solvent. Solvent generally used in this field can be used. Examples of the solvent include glycol ether esters such as ethyl cellosolve acetate, methyl cellosolve acetate and propylene glycol monomethyl ether acetate; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. One of these solvents can be used singly or two or more of the solvents can be used in combination.

The resist film formed by applying the resist solution on a substrate and drying is subjected to exposure treatment for patterning, then to heat treatment for promoting protective group-eliminating reaction and finally developed with an alkaline developer. The alkaline developer used here may be any aqueous alkaline solution used in this field. An aqueous solution of tetramethyl ammonium hydroxide or (2-hydroxyethyl)trimethyl ammonium hydroxide (common name: choline) is generally used as a developer.

EXAMPLES

The present invention will now be described in more detail referring to Examples, which should not be construed as a limitation upon the scope of the invention. In Examples, % and part for representing the content or amount to be used is weight based unless otherwise specified. The weight average molecular weight is a value obtained by gel permeation chromatography using polystyrene as the standard substance.

Synthetic Example 1 for Monomer (Synthesis of 2-methyl-2-adamantyl methacrylate)

Into a reaction vessel were charged 83.1 parts of 2-methyl-2-adamantanol and 101 parts of triethylamine, and 200 parts of methyl isobutyl ketone was added thereto to form a solution. To this solution was added dropwise 78.4 parts of methacryloyl chloride (1.5 mole based on 2-methyl-2-adamantanol). The solution was stirred at room temperature for about 10 hours. After filtration, the organic layer was washed with 5% aqueous sodium hydrogen carbonate solution and then washed twice with water. The organic layer was concentrated and distilled under reduced pressure to give 2-methyl-2-adamantyl methacrylate represented by the following formula:

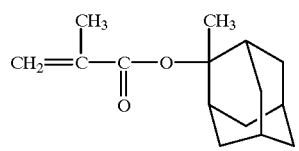

Synthetic Example 2 for Monomer (Synthesis of 2-ethyl-2-adamantyl methacrylate)

A solution was prepared by adding 50 parts of diethyl ether to 31.1 parts of 2-adamantanone. While keeping the temperature of the solution at or under 10° C., 200 ml of a diethyl ether solution containing ethyl lithium at a concentration of 1.14 mole/liter was added dropwise thereto. The solution was stirred at 0° C. for 2 hours, and then, while keeping the temperature of the solution at or under 10° C., 26.2 parts of methacryloyl chloride (1.2 mole based on 2-methyl-2-adamantanol) was added dropwise. After the completion of addition, the solution was stirred at room temperature for 12 hours. Then precipitated inorganic salts were removed by filtration. The organic layer was washed with 5% aqueous sodium hydrogen carbonate solution and then washed twice with water. The organic layer was concentrated and distilled under reduced pressure to give 2-ethyl-2-adamantyl methacrylate represented by the following formula:

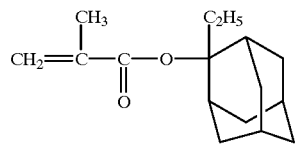

Synthetic Example 3 for Monomer (Synthesis of α-methacryloyloxy-γ-butyrolactone)

After charging 100 parts of α-bromo-γ-butyrolactone and 104.4 parts of methacrylic acid (2.0 times in mole based on α-bromo-γ-butyrolactone), a three times amount of methyl isobutyl ketone based on α-bromo-γ-butyrolactone was added thereto to form a solution. To this solution was added dropwise 153.6 parts of triethylamine (3.0 times in mole based on α-bromo-γ-butyrolactone). Then, the solution was stirred at room temperature for about 10 hours. After filtration, the organic layer was washed with 5% aqueous sodium hydrogen carbonate solution and then washed twice with water. The organic layer was concentrated to give α-methacryloyloxy-γ-butyrolactone represented by the following formula:

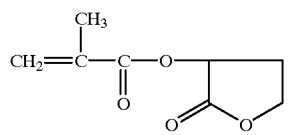

Synthetic Example 1 for Resin (Synthesis of resin A1)

After charging 2-methyl-2-adamantyl methacrylate and α-methacryloyl-γ-butyrolactone in a molar ratio of 5:5 (15.0 parts:11.7 parts), two times weight of methyl isobutyl ketone based on the total monomers was added thereto to form a solution. As an initiator, 2% by mole of azobisisobutyronitrile based on the total monomer amount was added thereto and the mixture was heated at 80° C. for about 8 hours. Then, the reaction solution was poured into a large amount of heptane to form precipitation and this procedure was repeated 3 times in total for purification. As the result, a copolymer having a weight average molecular weight of about 10,000 was obtained. The copolymer had structural units represented by the following formulae and is referred to herein as resin A1.

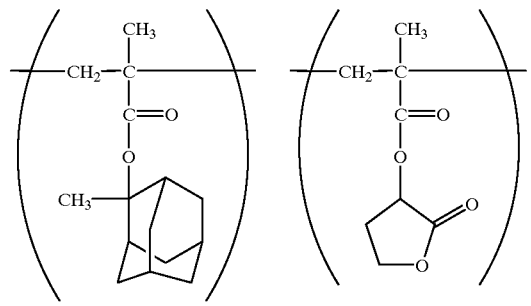

Synthetic Example 2 for Resin (Synthesis of resin A2)

The substantially same procedure in Synthetic Example 1 for Resin was repeated except that 2-ethyl-2-adamantyl methacrylate, 3-hydroxy-1-adamantyl methacrylate and α-methacryloyl-γ-butyrolactone were charged in a molar ratio of 5:2.5:2.5 (20.0 parts:9.5 parts:7.3 parts). As the result, a copolymer having a weight average molecular weight of about 9,200 was obtained. The copolymer had structural units represented by the following formulae and is referred to herein as resin A2.

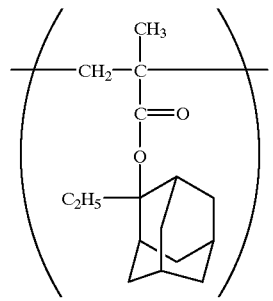

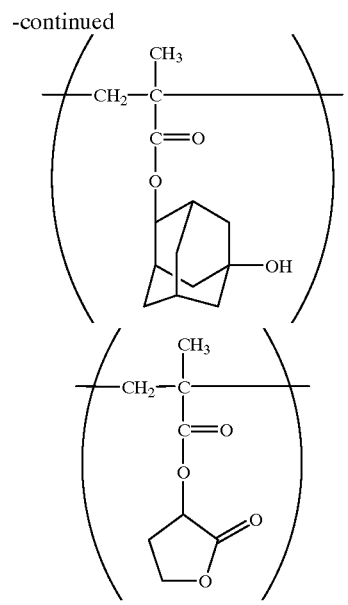

Synthetic Example 3 for Resin (Synthesis of resin A3)

After 2-adamanty-2-ethyl methacrylate, 1-adamantyl-3-hydroxy acrylate, norbornene and maleic anhydride were charged at a mol ratio of 2:2:3:3 (10.0 parts 9.0 parts 5.7 parts:5.9 parts), respectively, methylisobutylketone was added to the mixture in twice amount as much as the total weight of all the monomers. Thereafter, the mixture was heated to 80° C. in a nitrogen atmosphere. Then, azobisisobutyronitrile as an initiator was added, the amount being 3 mol % of the total of all the monomers, followed by heating the mixture at 80° C. for about 15 hr. Thereafter, the reaction mass was poured into a large amount of methanol for precipitation, and this procedure was repeated 3 times in total to obtain 17.1 parts of a copolymer having a weight-average molecular weight of about 12160 with a dispersion of 1.90. The copolymer had structural units represented by the following formulae and is referred to herein as resin A3.

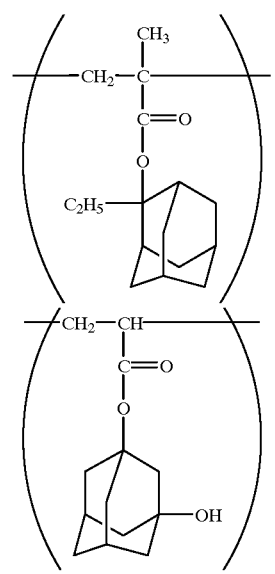

-continued

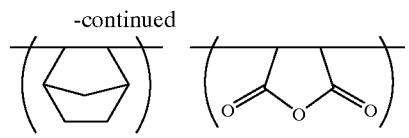

Synthetic Example 1 for Acid Generator (Synthesis of cyclohexylmethyl(2-oxocyclohexyl)sulfonium perfluorobutanesulphonate)

Into a four-necked flask, 3.2 parts of 2-(cyclohexylthio)cyclohexanone and 10.0 parts of nitromethane were charged and the mixture was cooled to 15° C. 19.2 parts of methyl iodide was added thereto and the mixture was stirred for 2 hr at the same temperature. Thereafter, a solution of 6.10 parts of silver pefluorobutanesulfonate dissolved in 200 parts of nitromethane was added dropwise gradually into the mixture, followed by stirring the mixture for 6 hours at the same temperature. Then, silver iodide precipitated in the previous step was filtered off and the silver iodide was rinsed with 32 parts of nitromethane. The filtrate and the rinsing liquid used were combined and concentrated to 8.4 parts. The concentrated liquid was added into 260 parts of diethylether. Deposited crystals were filtered off from the solution and rinsed with 30 parts of diethylether to obtain 1.35 parts of a target material at a yield of 17.1%. It was confirmed that this compound was cyclohexylmethyl(2-oxocyclohexyl)sulfonium perfluorobutanesulfonate by a $^1$H-NMR (on "GX-270" made by Nihon Denshi K.K.) analysis.

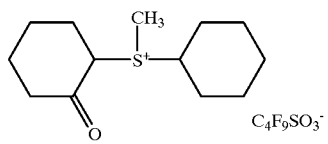

Melting point: 86 to 88° C. $^1$H-NMR spectrum (in a solvent CDCl$_3$ with Internal Reference Material tetramethylsilane); Chemical shift (δ or ppm). 1.15–2.32 (m, 15H); 2.52–2.83 (m, 3H); 2.83 (s, 1.5H); 2.96 (s, 1.5H); 3.57 (tt, 0.5H); 3.85 (tt, 0.5H); 5.36(dd, 0.5H); 5.50 (dd, 0.5H).

Synthetic Example 2 for Acid Generator (Synthesis of cyclohexylmethyl(2-oxocyclohexyl)sulfonium perfluorooctanesulphonate)

Into a four-necked flask, 4.25 parts of 2-(cyclohexylthio)cyclohexanone and 13.0 parts of nitromethane were charged and the mixture was cooled to 15° C. 25.5 parts of methyl iodide was added thereto and the mixture was stirred for 2 hr at the same temperature. Thereafter, a solution of 12.14 parts of silver pefluorooctanesulfonate dissolved in 750 parts of nitromethan was added dropwise gradually into the mixture, followed by stirring the mixture for 18 hours at the same temperature. Then, silver iodide precipitated in the previous step was filtered off and the silver iodide was rinsed with 40 parts of nitromethane. The filtrate and the rinsing liquid used were combined and concentrated to 15.1 parts. The concentrated liquid was added into 600 parts of diethylether. Deposited crystals were filtered off from the solution and rinsed with 50 parts of diethylether to obtain 6.22 parts of a target material at a yield of 42.8%. It was confirmed that this compound was cyclohexylmethyl(2-oxocyclohexyl)sulfonium perfluorooctanesulfonate by a $^1$H-NMR analysis.

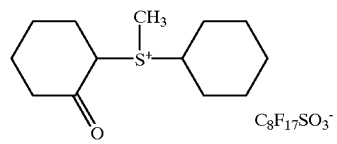

$^1$H-NMR spectrum (in a solvent CDCl$_3$ with Internal Reference Material tetramethylsilane); Chemical shift (δ or ppm). 1.15–2.32 (m, 15H); 2.52–2.83 (m, 3H); 2.83 (s, 1.5H); 2.95 (s, 1.5H); 3.58 (tt, 0.5H); 3.86 (tt, 0.5H); 5.38 (dd, 0.5H); 5.51 (dd, 0.5H).

Synthetic Example 3 for Acid Generator (Synthesis of 4-methylphenyldiphenylsulfonium perfluorooctanesulfonate)

Into a four-necked flask were charged 8.0 parts of diphenylsulfoxide and 80.0 parts of toluene, and the mixture was cooled to 2° C. Then, 16.6 parts of trifluoroacetic anhydride and 19.8 parts of perfluorooctanesulfonic acid were added and the mixture was stirred at the same temperature for 30minutes. After standing, the lower layer was concentrated and diluted with 340 parts of chloroform. The obtained chloroform solution was washed 6 times with 85 parts of ion-exchange water and concentrated to give 27.7 parts of 4-methylphenyldiphenylsulfonium perfluorooctanesulfonate.

Then, resist compositions were prepared using the following acid generators and the composition were evaluated.

Acid Generator B1:
  cyclohexylmethyl(2-oxocyclohexyl)sulfonium perfluoromethanesufonate ("CMS-105" made by Midori Chemical)

Acid Generator B2:
  cyclohexylmethyl(2-oxocyclohexyl)sulfonium perfluorobutanesufonate (a product of Synthetic Example 1 for Acid Generator)

Acid Generator B3:
  cyclohexylmethyl(2-oxocyclohexyl)sulfonium perfluorooctanesufonate (a product of Synthetic Example 2 for Acid Generator)

Acid Generator C1:
  4-methylphenyldiphenylsulfonium perfluoroocthanesulfonate (a product of Synthetic Example 3 for Acid Generator)

Acid Generator C2:
  4-methylphenyldiphenylsulfonium perfluoromethanesulfonate ("MDS-205", manufactured by Midori Chemical)

Example 1

Resist solution was prepared by mixing the components shown in the following Table, followed by filtration of the resulting solutions through a fluorine resin filter having a pore size of 0.2 μm.

TABLE 1

| Component | (parts) |
| --- | --- |
| Resin A2 | 10 |
| Acid generator B1 | 0.5 |
| Acid generator C1 | 0.5 |
| Quencher: 2,6-diisopropyl aniline | 0.015 |

TABLE 1-continued

| Component | (parts) |
|---|---|
| Solvent: | |
| propylene glycol monomethyl ether acetate | 47.5 |
| γ-butyrolactone | 2.5 |

"DUV-30" made by Brewer Co. was coated on a silicon wafer and the wafer coated was baked at of 215° C. for 60 sec, to form an organic anti-reflection film of 1,600 Å in thickness. The above described resist solution was spin-coated so as to obtain a dried film of 0.39 μm in thickness. After coating of the resist solution, the wafer was prebaked on a direct hot plate at 100° C. for 60 sec A line and space pattern was projected on the wafer on which the resist film was formed using an ArF excimer laser aligner ("NSRArF", NA=0.55 and σ=0.6, made by Nicon) with stepwise changing in exposure dose. After the exposure, the wafer was subjected to post-exposure baking on a hot plate at 115° C. for 60 sec, followed by paddle development with 2.38% aqueous solution of tetramethylammonium hydroxide for 60 sec. A pattern after the development was observed with a scanning electron microscope to investigate an effective sensitivity and resolution by the following ways. The results were 2.2 mJ/cm² in effective sensitivity and 0.16 μm in resolution:

Effective sensitivity was indicated by a minimum exposure dose which gives 1:1 line-and-space pattern of 0.18 μm.

Resolution: This is shown in the minimum size which gives line-and-space pattern splitted at the amount of exposure giving the effective sensitivity.

Further, an above described resist solution was coated on a quartz glass wafer and prebaked so as to obtain a resist film having thickness of 0.39 μm after prebaking according to the same conditions as the above described. A transmittance at a wavelength of 193 nm of the resist film was measured with a spectrophotometer. As a result, the transmittance was 62%. As described above, the resist not only indicated a high transmittance, but was also excellent in sensitivity and resolution.

Examples 2–7 and Comparative Examples 1–2

Resist solutions were prepared by mixing the components shown in the following Table, followed by filtration of the resulting solutions through a fluorine resin filter having a pore size of 0.2 μm.

TABLE 2

| Component | (parts) |
|---|---|
| Resin (denomination is shown in Table 3) | 10 |
| Acid generator (denomination is shown in Table 3) | * |
| Quencher: 2,6-diisopropyl aniline | 0.015 |
| Solvent: | |
| propylene glycol monomethyl ether acetate | 47.5 |
| γ-butyrolactone | 2.5 |

*The amounts are shown in Table 3.

"DUV-30" made by Brewer Co. was coated on a silicon wafer and the wafer coated was baked at of 215° C. for 60 sec, to form an organic anti-reflection film of 1,600 Å in thickness. The above described resist solution was spin-coated so as to obtain a dried film of 0.39 μm in thickness. After coating of the resist solution, the wafer was prebaked on a direct hot plate at 120° C. for 60 sec. A line and space pattern was projected according to the same manner as in Example 1. After the exposure, the wafer was subjected to post-exposure baking on a hot plate at 120° C. for 60 sec, followed by paddle development with 2.38% aqueous solution of tetramethylammonium hydroxide for 60 sec. A pattern after the development was observed with a scanning electron microscope to investigate an effective sensitivity and resolution by the same ways as in Example 1. In Example 7, DUV-30J was used in place of DUV-30, and the temperature of post-exposure baking was 115° C.

Further, an above described resist solution was coated on a quartz glass wafer and prebaked so as to obtain a resist film having thickness of 0.39 μm after prebaking according to the same conditions as the above described. A transmittance at a wavelength of 193 nm of the resist film was measured with a spectrophotometer.

The results are shown in Table 3.

TABLE 3

| Example No. | Resin | Acid generator (parts) | Effective sensitivity mJ/cm² | Resolution μm | Transmittance % |
|---|---|---|---|---|---|
| Example 2 | A2 | B2 (1.0) | 58 | 0.16 | 72 |
| Example 3 | A2 | B2 (0.2) + C1 (0.25) | 42 | 0.15 | 63 |
| Example 4 | A2 | B3 (0.2) + C1 (0.25) | 46 | 0.15 | 58 |
| Example 5 | A2 | B2 (0.4) + C1 (0.2) | 42 | 0.15 | 62 |
| Example 6 | A1 | B2 (0.2) + C1 (0.25) | 48 | 0.15 | 60 |
| Example 7 | A3 | B2 (0.2) + C1 (0.25) | 47 | 0.16 | 61 |
| Comparative example 1 | A1 | C2 (0.1) | 70 | 0.17 | 63 |
| Comparative example 2 | A2 | C2 (0.1) | 62 | 0.17 | 62 |

As being apparent from the results of Example 1 and Table 3, the resists of the examples were excellent in sensitivity and resolution as compared with other resists having the transmittance of the same order. Furthermore, the resist of Example 2 in which cyclohexylmethyl(2-oxocyclohexyl)sulfonium perfluorobutanesulfonate was singly used as an acid generator showed a high transmittance at a wavelength of 193 nm even though the acid generator was used in a large amount. Therefore, the resist is effective for improvement of a resist pattern profile since ArF excimer laser light used for exposure is hard to be absorbed.

Example 8

Wafers (basic substrate) having a silicon nitride film of 1,800-angstrom in thickness were surface-treated with hexamethylsilazane according to a conventional method. Then, the resist solutions prepared in Examples 3 and 5 were applied on the wafers in a manner similar to that described above so as to form resist films having thickness of 0.5 μm after drying. After patterning, the substrate-dependence was assessed by observing cross-section shapes of the patterns with scanning electronic microscope. The results showed that the patterns obtained had good profiles without bottom-tailing.

As described above, the resists in Examples were improved in resolution and also gave a good profile on a low reflection substrate, as compared with the resists in Comparative Examples in which 4-methylphenyldiphenylsulfonium perfluoromethanesulfonate was used. In addition, the resists prepared in these Examples are less liable to give a profile with bottom-tailing even when applied on a basic substrate.

Examples 9–11

Resist solution was prepared by mixing the components shown in the following Table, followed by filtration of the resulting solutions through a fluorine resin filter having a pore size of 0.2 µm.

TABLE 4

| Component | Example 9 (parts) | Example 10 (parts) | Example 11 (parts) |
|---|---|---|---|
| Resin A2 | 10 | 10 | — |
| Resin A4* | — | — | 10 |
| Acid generator B1 | 0.5 | 0.5 | 0.5 |
| Acid generator C1 | 0.2 | 0.2 | 0.2 |
| Quencher: | | | |
| 2,6-diisopropyl aniline | 0.015 | 0.015 | 0.015 |
| 2,6-lutidine | — | 0.01 | — |
| Solvent: | | | |
| propylene glycol monomethyl ether acetate: | 57 | 57 | 57 |
| γ-butyrolactone | 3 | 3 | 3 |

*Resin 4 is a copolymer of 2-methyl-2-adamantyl methacrylate and β-methacryloyloxy-γ-butyrolactone at a mol ratio of 47.7 to 52.3 and a weight-average molecular weight of the resin 4 is about 8,400.

Among these, resist solutions of Examples 9 and 10 each were divided in halves and one was stored at 60° C. for 24 hours, followed by cooling to 23° C. over 1 hour, while the other was stored at 23° C. for the time period. The resist solutions treated in such ways were subjected to the following tests. The resist solution of Example 11 was subjected to the tests without pretreatment mentioned above.

"DUV-30" made by Brewer Co. was coated on a silicon wafer and the wafer coated was baked at of 215° C. for 60 sec. to form an organic anti-reflection film of 1,600 Å in thickness. The above described resist solution was spin-coated so as to obtain a dried film of 0.39 µm in thickness. After coating of the resist solution, the wafer was prebaked on a direct hot plate at 110° C. for 60 sec. A line and space pattern was projected according to the same manner as in Example 1. After the exposure, the wafer was subjected to post-exposure baking on a hot plate at 115° C. for 60 sec, followed by paddle development with 2.38% aqueous solution of tetramethylammonium hydroxide for 60 sec. A pattern after the development was observed with a scanning electron microscope to investigate an effective sensitivity and resolution by the same ways as in Example 1.

Further, an above described resist solution was coated on a quartz glass wafer and prebaked so as to obtain a resist film having thickness of 0.39 µm after prebaking according to the same conditions as the above described. A transmittance at a wavelength of 193 nm of the resist film was measured with a spectrophotometer.

The results are shown In Table 5.

TABLE 5

| Example No. | Resin | Effective sensitivity mJ/cm$^2$ 1) | 2) | Resolution µm 1) | 2) | Transmittance % 1) | 2) |
|---|---|---|---|---|---|---|---|
| Example 9 | A2 | 19 | 13 | 0.16 | 0.16 | 61 | 58 |
| Example 10 | A2 | 20 | 18 | 0.16 | 0.16 | 61 | 61 |
| Example 11 | A2 | 13 | — | 0.16 | — | 71 | — |

1) Stored at 23° C.
2) Stored at 60° C.

The resists of Examples 9 to 11 were good in sensitivity, resolution and transmittance. Particularly, in Example 10 in which 2,6-lutidine was used as quencher, changes in sensitivity and transmittance were small after an accelerated test carried out at 60° C. for 24 hours. Thus, storage stability was improved. Further, the resist of Example 11 in which Resin A4 was used was higher in sensitivity, and high in transmittance at wavelength of 193 nm.

According to the present invention, resist compositions using a specific acid generator are good in resolution and in addition, and provide a good pattern profile under exposure using light of wavelength of 220 nm or shorter, for example, ArF excimer laser light even when applied on a basic substrate or a low reflectance substrate, thereby exerting an effect of less substrate dependence.

What we claim is:
1. A chemical amplification type positive resist composition which comprises

(1) an acid generator comprising
an aliphatic sulfonium salt represented by the following formula (I):

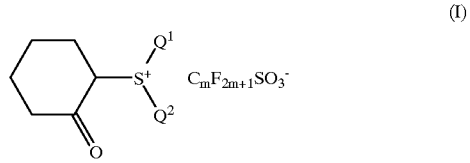

(I)

wherein $Q^1$ represents an alkyl group, $Q^2$ represents an alkyl or a residue of an alicyclic hydrocarbon and m represents an integer of 1 to 8; and at least one onium salt selected from triphenylsulfonium salts represented by the following formula (IIa) and diphenyiodonium salts represented by the following formula (IIb):

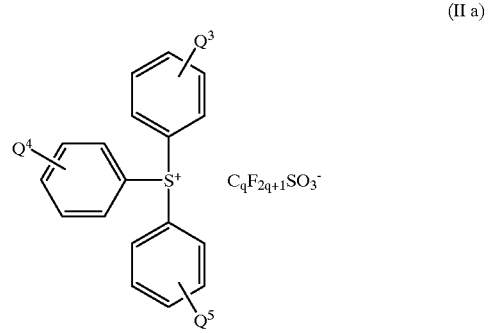

(II a)

(IIb)

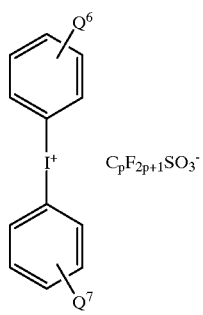

wherein $Q^3$, $Q^4$, $Q^5$, $Q^6$ and $Q^7$ each independently represent a hydrogen atom, a hydroxyl group, an alkyl group having 1 to 6 carbon atoms, an alkoxy group having 1 to 6 carbon atoms, and q and p represent a integer of 4 to 8; and (2) a resin which has a polymerization unit with a group unstable to an acid, and is insoluble or barely soluble in alkali by itself but changes soluble in alkali by an action of the acid.

2. The chemical amplification type positive resist composition according to claim 1, wherein m in the formula (I) is an integer of 4–8.

3. The chemical amplification type positive resist composition according to claim 1, wherein the weight ratio of the aliphatic sulfonium salt represented by the formula (I) to the onium salt selected from triphenylsulfonium salts represented by the formula (IIa) and diphenyliodonium salts represented by the formula (IIb) is about 9:1 to 1:9.

4. A chemical amplification type positive resist composition which comprises
(1) an acid generator comprising
an aliphatic sulfonium salt represented by the following formula (Ia):

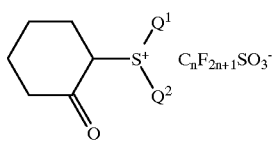
(Ia)

wherein $Q^1$ represents an alkyl group, $Q^2$ represents an alkyl or a residue of an alicyclic hydrocarbon and n represents an integer of 4 to 8; and
(2) a resin which has a polymeriation unit with a group unstable to an acid, and is insoluble or barely soluble in alkali by itself but changes soluble in alkali by an action of the acid.

5. The chemical amplification type positive resist composition according to claim 1 or 4, wherein the ratio of the polymerization unit with a group unstable to an acid to all polymerization units of the resin is in the range of 10 to 80 mol %.

6. The chemical amplification type positive resist composition according to claim 1 or 4, wherein the polymerization unit with a group unstable to an acid is a unit introduced from 2-alkyl-2-adamantyl (meth)acrylate.

7. The chemical amplification type positive resist composition according to claim 6, wherein 2-alkyl-2-adamantyl (meth)acrylate is selected from 2-methyl-2-adamantyl methacrylate and 2-ethyl-2-adamantyl methacrylate.

8. The chemical amplification type positive resist composition according to claim 1 or 4, wherein (2) the resin further has at least one selected from a polymerization unit introduced from 3-hydroxy-1-adamantyl (meth)acrylate and a polymerization unit introduced from (meth)acryloyloxy-γ-butyrolactone wherein the lactone ring may be optionally substituted with an alkyl group.

9. The chemical amplification-type positive resist composition according to claim 1 or 4, wherein (2) the resin is a copolymer having a polymerization unit with a group unstable to an acid and a polymerization unit selected from a polymerization unit introduced from 3-hydroxy-1-adamantyl (meth)acrylate and a polymerization unit introduced from (meth)acryloyloxy-γ-butyrolactone wherein the lactone ring may be optionally substituted with an alkyl group.

10. The chemical amplification type positive resist composition according to claim 1 or 4, wherein (2) the resin is a terpolymer having a polymerization unit with a group unstable to an acid, a polymerization unit introduced from 3-hydroxy-1-adamantyl (meth)acrylate and a polymerization unit introduced from (meth)acryloyloxy-γ-butyrolactone wherein the lactone ring may be optionally substituted with an alkyl group.

11. The chemical amplification type positive resist composition according to claim 8, wherein the (meth)acryloyloxy-γ-butyrolactone wherein the lactone ring may be optionally substituted with an alkyl group is selected from α-(meth)acryloyloxy-γ-butyrolactone wherein the lactone ring may be optionally substituted with an alkyl group and β-(meth)acryloyloxy-γ-butyrolactone wherein the lactone ring may be optionally substituted with an alkyl group.

12. The chemical amplification type positive resist composition according to claim 8, wherein (2) the resin further has a polymerization unit introduced from 2-norbornene and a polymerization unit introduced from an aliphatic unsaturated dicarboxylic anhydride.

13. The chemical amplification type positive resist composition according to claim 1, which further comprises an amine compound, as a quencher.

14. The chemical amplification type positive resist composition according to claim 13, wherein the amine compound comprises a 2,6-dialkylpyridine compound represented by the following formula (X):

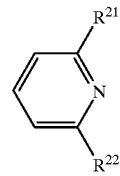
(X)

wherein $R^{21}$ and $R^{22}$ independently represent an alkyl group having 1 to 4 carbon atoms.

15. An aliphatic sulfonium salt represented by the following formula (Ia):

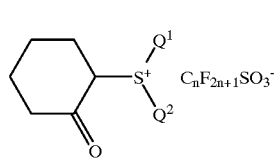
(Ia)

wherein $Q^1$ represents an alkyl group, $Q^2$ represents an alkyl or a residue of an alicyclic hydrocarbon and n represents an integer of 4 to 8.

16. The aliphatic sulfonium salt according to claim 15, wherein $Q^2$ represents a cycloalkyl group.

* * * * *